United States Patent [19]

Zang et al.

[11] Patent Number: 5,314,486
[45] Date of Patent: May 24, 1994

[54] NON-CONSTRAINED TOTAL JOINT SYSTEM

[75] Inventors: Kerry Zang, Paradise Valley, Ariz.; Randall J. Huebner, Aloha, Oreg.

[73] Assignee: MicroAire Surgical Instruments, Inc., Valencia, Calif.

[21] Appl. No.: 7,370

[22] Filed: Jan. 19, 1993

Related U.S. Application Data

[63] Continuation of Ser. No. 720,709, Jun. 25, 1991, abandoned.

[51] Int. Cl.$^5$ .............................. A61F 2/42; A61F 2/30
[52] U.S. Cl. .......................................... 623/21; 623/18
[58] Field of Search ........................ 623/21, 20, 18, 19

[56] References Cited

U.S. PATENT DOCUMENTS

| | | | |
|---|---|---|---|
| 3,889,300 | 6/1975 | Smith | 623/21 |
| 4,021,864 | 5/1977 | Waugh | 623/21 |
| 4,156,296 | 5/1979 | Johnson et al. | 623/21 |
| 4,470,158 | 9/1984 | Pappas et al. | 623/20 |
| 4,908,031 | 3/1990 | Frisch | 623/21 |
| 5,061,288 | 10/1991 | Berggren et al. | 623/18 |

*Primary Examiner*—David Isabella
*Assistant Examiner*—Debra S. Brittingham
*Attorney, Agent, or Firm*—Whitham & Marhoefer

[57] ABSTRACT

A non-constrained total joint prosthetic replacement device for metatarso-phalangeal joint. A first component comprises a convex-bearing surface and a rearwardly projecting stem configured to be received in the resected metatarsal bony shaft, and a second component includes a concave-bearing surface and a stem configured to be received within the resected phalangeal bony shaft. A non-bearing intermediate land offsets the convex-bearing surface of the first component from the stem, allowing a full range of anatomical motion notwithstanding the presence of bony overgrowth.

14 Claims, 4 Drawing Sheets

NON-CONSTRAINED TOTAL JOINT SYSTEM

CROSS-REFERENCE TO RELATED APPLICATION

This application is a continuation of application Ser. No. 07/720,709 filed Jun. 25, 1991, now abandoned.

FIELD OF THE INVENTION

The present invention relates to non-constrained total joint systems and particularly to prosthetic devices for replacement of metatarso-phalangeal joints.

BACKGROUND OF THE INVENTION

In general, prostheses for replacing defective natural joints between bony shafts are well known. One example of a total joint replacement for the metatarsal phalangeal joint of the foot employs a collared hinge with opposing integral stems, all formed of silicone. To install such a device, an incision is made and the metatarsal and phalangeal bones exposed and resected. Axial channels are formed in the intramedullary canals of the proximal phalanx and metatarsal. The stems are then disposed in the channels, the collars seated against the ends of the bones, and the incision closed. An example of such a silicone hinge replacement is the Sutter Hinged Great Toe Joint Implant, marketed by Sutter Biomedical, Inc.

Non-constrained total joint replacement systems are also known. In the context of the metatarsophalangeal joint, such systems typically include separate metatarsal and phalangeal components configured to be disposed on the ends of the respective resected bony shafts and maintained in place by the soft tissue surrounding the bones.

One type of such non-constrained system employs a metatarsal component including a cap with a rearwardly projecting stem. The stem is received in a channel formed in the intramedullary canal of the metatarsal, and the cap, in effect, covers the end of the metatarsal head, wrapping around the sides of the metatarsal. Resection of the metatarsal in a plurality of planes (i.e., faceting themetatarsal head) is typically required for disposition of the metatarsal cap. The phalangeal component comprises a disc-shaped base with a curved bearing surface and a rearwardly projecting stem. The metatarsal component is typically formed of biocompatible metal, and the phalangeal portion formed of polyethylene or of polyethylene backed with metal.

Other non-constrained systems employ a metatarsal component comprising a domed head with a rearwardly projecting rectangular cross-section stem. The head includes a convex, part-spherical bearing surface extending to the periphery of the metatarsal component and defining the maximum transverse dimension of the metatarsal component. No portion of the metatarsal component extends transversely beyond the bearing surface. The phalangeal component includes a concave part-spherical bearing surface and a rearwardly projecting stem of generally rectangular cross-section. The radii of the respective bearing surfaces are equal. However, the surface area of the convex bearing surface on the metatarsal component is noticeably larger than the surface area of the concave bearing surface on the phalangeal component. The metatarsal component is formed of a substantially physiologically inert metal, such as orthochrome, and the phalangeal component formed of polyethylene. When implanted, the stems of the metatarsal and phalangeal components are received in respective channels formed in the medullary channels of the bones.

Such prior art devices, when implanted, dispose the convex bearing surface immediately and contiguously adjacent to the bone. The present inventors have found that this tends to limit the range of permitted motion in the joint, and renders the system susceptible to bony overgrowth. Such bony overgrowth tends to further limit the permissible range of motion in the joint. Further, various of such prior art systems employ a metatarsal component having a concave part-spherical rear surface. The metatarsal head is craterized to form a recess to receive the metatarsal component so that the edge of the bearing surface abuts metatarsal bone. Such an arrangement is not only particularly susceptible to bony overgrowth, but tends to initiate a periosteal reaction that promotes bony overgrowth. In addition, during extremes of flexion and extension, the phalangeal component tends to ride off of the metatarsal component onto part of the actual articular surface of the metatarsal head. The polyethylene component thus tends to articulate with already deceased cartilage, often exacerbating a diseased condition and breaking down the actual articular surface of the metatarsal head in the vicinity of the metatarsal component.

Examples of prior art non-constrained systems are the "Total Toe System" marketed by Biomet, Inc. and the system described in U.S. Pat. No. 4,156,296 issued May 29, 1979 to Johnson, et al.

SUMMARY OF THE INVENTION

The present invention provides a non-constrained total joint system which provides a full anatomical range of motion, without impingement on or articulation with the actual anatomical structures, and is relatively unsusceptible to bony overgrowth. In general, the system employs first and second, e.g., metatarsal and phalangeal, components. The first component comprises a head and a rearwardly projecting stem configured to be received in the end of the bony shaft. The head includes a convex-bearing surface, and a non-bearing intermediate portion interposed between the stem and the convex-bearing surface, offsetting the convex-bearing surface from the bony shaft end. The second component includes an articulating element and a stem configured to be received in the end of the second cooperating bony shaft. The articulating element includes a concave-bearing surface having a surface area a predetermined amount less than that of the convex surface. The intermediate non-bearing portion provides clearance against impingement and tends to make the joint less susceptible to disfunction due to bony overgrowth.

In accordance with another aspect of the present invention, the side periphery of the articulating element bounding the concave-bearing surface is beveled to a predetermined angle. Such bevel, particularly in cooperation with the intermediate portion, permits the full anatomical range of motion without impingement on anatomical structures.

In accordance with another feature of the present invention, intercapsular synovial fluid is employed to moisten and lubricate the bearing surfaces of the prosthesis.

BRIEF DESCRIPTION OF THE DRAWING

A preferred exemplary embodiment of the present invention will hereinafter be described in conjunction with the appended drawings, wherein like designations denote like elements and.

DETAILED DESCRIPTION OF A PREFERRED EXEMPLARY EMBODIMENT

Figure 1:
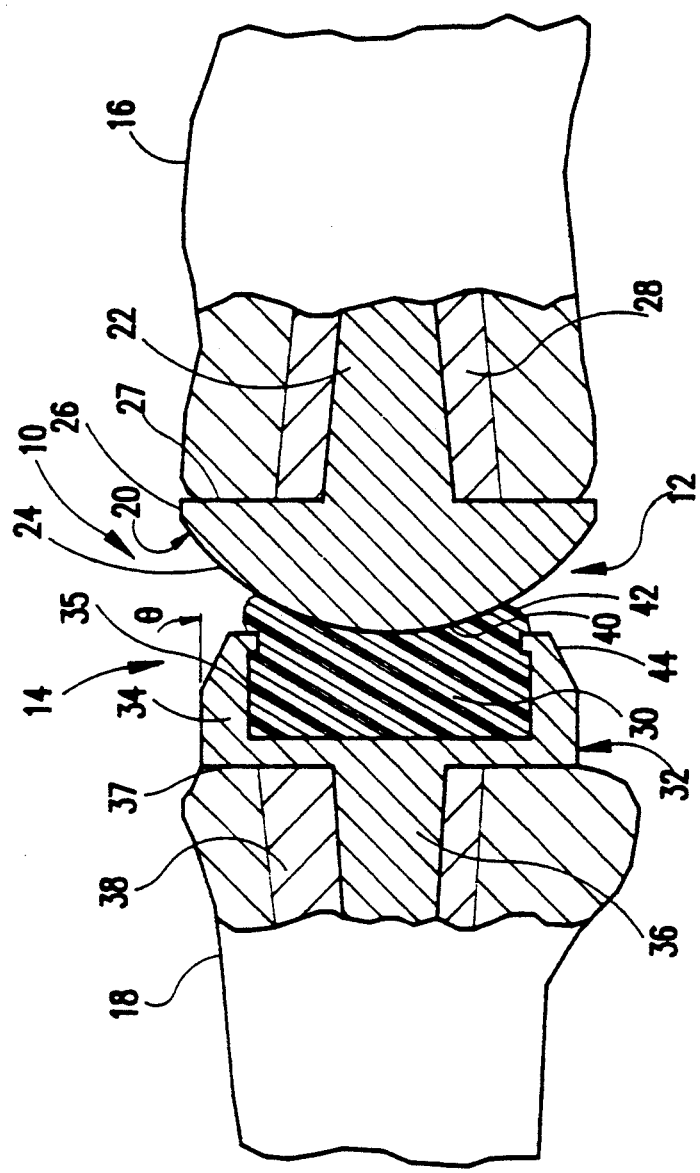
FIG. 1 is a partially sectioned front view of a non-constrained joint system in accordance with the present invention installed in respective bony shafts.

Referring now to FIG. 1, a non-constrained total joint system in accordance with the present invention comprises first and second components, e.g., a metatarsal component 12 and a phalangeal (articulating) component 14, adapted to be received on the ends of respective resected bony shafts, e.g., the metatarsal 16 and phalangeal 18 bones of the big toe. When joint system 10 is implanted in bony shafts 16 and 18, the surrounding soft tissue structure (not shown) maintains component 12 on component 14 in cooperating position.

Figure 2A:
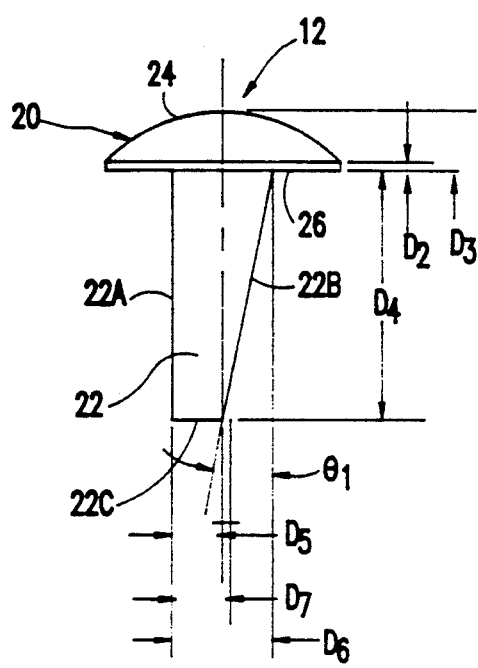
FIGS. 2A, 2B and 2C are front, side, and bottom views of the metatarsal component of FIG. 1.
Figure 2B:
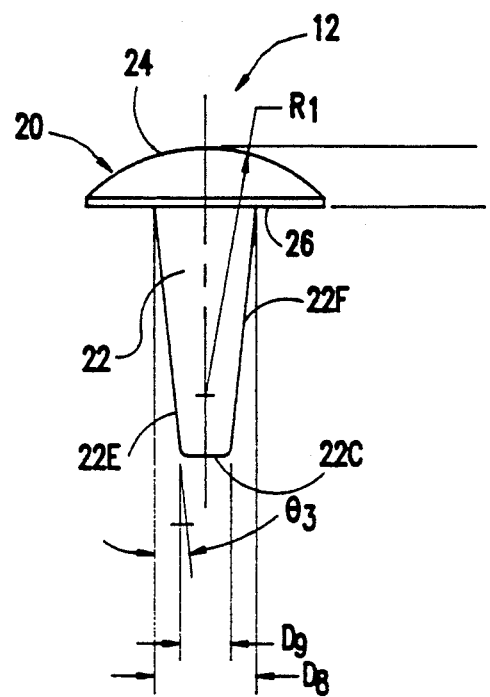
Figure 2C:
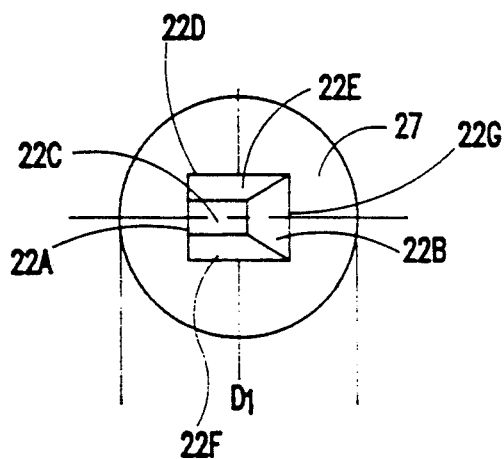

Metatarsal component 12 comprises a head 20 and a rearwardly projecting stem 22. Head 20 includes a convex bearing surface 24, a non-bearing intermediate portion, e.g., land 26, and a generally flat rear surface 27. Stem 22 is configured to be received in a channel formed in the intramedullary canal 28 of bony shaft 16, with rear surface 27 abutting the resected end of metatarsal bony shaft 16. Non-bearing intermediate portion, e.g., land 26, offsets convex bearing surface 24 from the end of bony shaft 16 by a predetermined amount. Component 12 is suitably formed as an integral unit of biocompatible metal, e.g., cobalt chrome, and will be more fully described in conjunction with FIGS. 2A–2C.

Figure 3A:
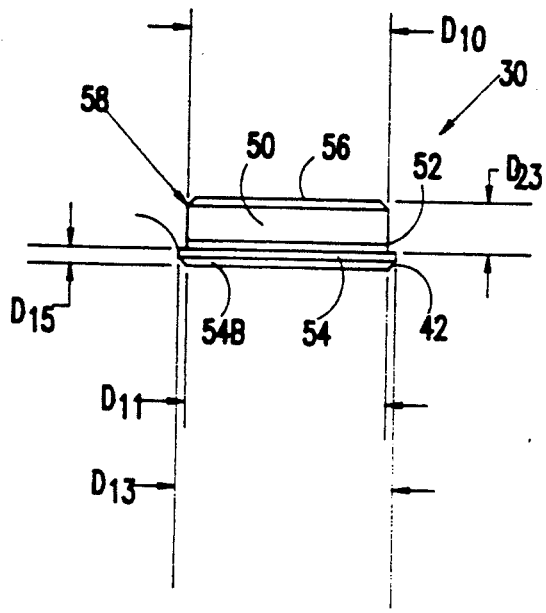
FIGS. 3A and 3B are front and front cross-sectional views of the phalangeal insert of the system of FIG. 1.

Phalangeal component 14 preferably comprises an intermediate bearing insert 30 formed of biocompatible plastic, e.g., ultra high molecular weight polyethylene, and a base unit 32 formed of biocompatible metal, e.g., titanium. As will be more specifically described in connection with FIGS. 3A-3C, insert 30 is suitably relatively thin, including a generally cylindrical rear portion and a frustro-conical forward section with a concave bearing surface 40 in the front face thereof configured for cooperation with convex bearing surface 24. A beveled forward side periphery 42 is presented in the vicinity of surface 40. Concave surface 40 is of a surface area smaller, by a predetermined amount, than the surface area of convex surface 24. Base unit 32 comprises a receptacle portion 34 and a rearwardly projecting stem 36. Receptacle portion 34 includes a forward-opening lipped chamber 35, a generally circular rear surface 37 and a beveled forward peripheral side surface 44. Insert 30 is configured to be received and secured (press fit) in receptacle 34, with concave surface 40 outward. The forward side periphery 42 of insert 30 and forward side periphery 44 of base receptacle 32 are each beveled to a predetermined angle $\theta_1$.

Stem 36 extends rearwardly from rear surface 37, and is configured to be received in a channel formed in the intramedullary canal 38 of phalanx 18 with rear surface 37 of base unit 34 abutting the resected end of bony shaft 18. When joint system 10 is implanted in bony shafts 16 and 18, the surrounding soft tissue structure (not shown) causes concave bearing surface 40 to ride on convex bearing surface 24.

Joint system 10 provides the full anatomical range of motion, e.g., upwards of 60° in the sagittal plane, and maintains an approximation of the true anatomical center of motion, not only through flexion and extension of the toe, but also through pronation and supernation encountered by the great toe during walking. Use of an intermediate portion, e.g., land 26, to offset convex surface 24 from the end of bone 16 facilitates use of a convex bearing surface 24 having a relatively large radius of curvature, i.e., relatively flat (approximating that of the anatomic articulating surface, while, at the same time, providing sufficient clearance for articulating component 14 as against bony shaft 16 and possible bony overgrowth. Full anatomical range of motion and approximation of the true anatomical center of motion, without impinging on any anatomical structure, is provided for by using, particularly in conjunction with the offset provided by land 26, an articulating component 14 with a concave surface 40 having a relatively small surface area, and having a beveled forward side periphery. The relative dimensions of bearing surfaces 24 and 40 are such that with the joint at the upper range of maximum anatomical flexion, as defined by the surrounding soft tissue structure, concave bearing surface 40 is still substantially riding upon the convex bearing surface 24, or overhangs the bearing surface only by a predetermined limited amount, as will be explained. The bevel of side peripheral surfaces 42 and 44 ensures that there is no impingement upon the metatarsal anatomical structure, or any bony overgrowth or soft tissue ingrowth that may occur. It is desirable to make bevel angle $\theta_1$ as large as possible, e.g., on the order of 20° to 35°, and preferably approximately 30°, without losing stability of contact between bearing surfaces, i.e., without decreasing the diameter of the concave bearing surface to below a predetermined minimum, e.g., in the range of from 5 to 15 millimeters (mm), and preferably 11 to 13 mm.

Joint system 10 can be installed employing a relatively simple procedure: an incision is made over the joint; bones 16 and 18 are exposed; a single straight planar resection is effected at the end of each bone, thereby removing the anatomical joint; axial channels are formed in intramedullary canals 28 and 38; stems 22 and 26 of components 12 and 14 are pressed into the channels (with fixative as appropriate) until the rear surfaces 27 and 37 of the components abut against the resected ends of bones 16 and 18, respectively. The dimensions of components 12 and 14 are such that resection of a relatively small amount of bone material is required and the integrity of the soft tissue structures in the vicinity of the joint important for stability of the great toe, and in particular the flexer tendon group, can therefore be preserved. As noted above, the use of land 26 to offset convex bearing surface 24 from the end of bone 16 facilitates the use of a larger radius of curvature than would otherwise be possible, while still providing adequate clearance over anatomical structures and any bony overgrowth. This results in metatarsal head 20 having an overall height less than would otherwise be required. Further, the use of relatively thin polyethylene bearing insert 30 maintained within a shallow, but strong, metal base 32 provides a particularly stable, axially thin phalangeal component. In situ, insert 30 is largely encapsulated by metal; the bulk of insert 30 is retained within metal receptacle 32 and concave surface 40 is faced by metal bearing surface 24. There is no polyethylene-on-bone interface, or articulation. Thus, phalangeal component 14 can be thinner, yet better resist fragmentation and wear than a unitary polyethylene phalangeal component. Moreover, the stability and longevity of joint system 10 are substantially improved; metal-on-metal and bone-on-polyethylene contacts, which are subject to abrasive wear, are avoided. Use of metal stems 22 and 36, and flat metal rear surfaces 27 and 37, also promotes stability of the implant and bonding of components 12 and 14 to bones 16 and 18.

It is desirable that the respective diameters of rear surfaces 27 and 37 approximate, preferably by being at least equal to, the diameter of the corresponding re-sected bone end. The present inventors have found that the metatarso-phalangeal joint of the large majority of adult humans can be accommodated using combinations of two sizes (small and large) of metatarsal 12 and phalangeal 14 components. The small and large size phalangeal components 14 are designed to cooperate with both the small and large metatarsal components 12.

Referring now to FIGS. 1, 2A, 2B and 2C, metatarsal component 12 will be more specifically described. As previously noted, component 12 comprises head 20 and stem 22. Head 20 includes convex bearing surface 24 and an intermediate non-bearing portion, e.g., land 26. Convex bearing surface 24 is suitably in the form of the surface of a part sphere or part spheroid or ellipsoid having a major radius of curvature $R_1$, suitably in the range of from approximately 7 to 17 mm, preferably $9.53 \pm 0.05$ mm for a small, or $12.70 \pm 0.5$ mm for a large, component. Bearing surface 24 abuts and is contiguous with the intermediate non-bearing surface (land 26) in the embodiment of FIGS. 1, 2A, 2B and 2C. Land 26 is suitably cylindrical, with a diameter $D_1$ (FIG. 2C) and axial height $D_2$ (FIG. 2A), and defines a generally circular flat rear surface 27. Diameter $D_1$ suitably ranges from approximately 13 to 25 mm, preferably either approximately 15.88 mm for a small, or 18.80 mm for a large, component. Height $D_2$ suitably ranges from approximately 0.5 to 1.5 mm, preferably either approximately 0.83 mm for a small, or 0.91 mm for a large, component. The overall axial height $D_3$ of metatarsal head 20 is suitably on the order of 3 to 8 mm, and preferably approximately 5.08 mm.

Stem 22 projects axially from rear surface 27 to a predetermined distance $D_4$, of on the order of 16 mm, preferably approximately 15.75 mm for both small and large component 12. Stem 22 is preferably generally centered on rear surface 27, and exhibits a rectangular cross-section that decreases with distance from the juncture with rear surface 27. More specifically, the projection of stem 22 into the frontal plane (FIG. 2A) is a quadrilateral formed by respective opposing sides 22A and 22B, an end 22C and a juncture 22D with surface 27. Side 22A is disposed parallel to the central axis of component 12, i.e., perpendicular to rear surface 27, offset from the centerline by a predetermined distance $D_5$. Distance $D_5$ suitably ranges from approximately 3 to 4 mm, preferably approximately 3.18 mm for a small, or 3.81 mm for a large, component. Opposing side 22B is disposed at a predetermined angle $\eta_2$, e.g., on the order of 10° from the central axis. Stem 22 is suitably of a predetermined width $D_6$ at juncture 22D with rear surface 27. Width $D_6$ suitably ranges from approximately 5 mm to 9 mm, preferably approximately 6.35 mm for a small, or 7.82 mm for a large, component. End surface 22C of stem 22 is suitably parallel to rear surface 27, and is of predetermined width $D_7$, suitably in the range of from approximately 2.5 to 5.5 mm, and preferably approximately 3.58 mm for a small, or approximately 4.27 mm for a large, component.

The projection of stem 27 in the coronal plane (FIG. 2B) is a generally wedge-shaped quadrilateral formed by respective opposing sides 22E and 22F, end 22C and a juncture 22G with rear surface 27. Sides 22E and 22F are each tapered at a predetermined angle $\theta_3$, suitably on the order of 5° and preferably approximately 5.3°, from the axis of component 12. Stem 22 manifests a predetermined height $D_8$ at the juncture with rear surface 27, and tapers to a lesser height $D_9$ at end 22C. Height $D_8$ suitably ranges from approximately 5 to 9 mm, and preferably either approximately 5.23 mm for a small, or approximately 8.80 mm for a large, component. Height $D_9$ suitably ranges from approximately 2.25 to 3.5 mm, preferably approximately 2.54 mm for a small, and 3.05 mm for a large, component.

Referring now to FIGS. 1 and 3A, 3B and 3C, insert 30 will be more particularly described. Insert 30 is suitably formed as an integral unit of a biocompatible plastic such as ultra high molecular weight polyethylene, and includes the following respective contiguous, coaxially aligned sections: rear section 50; intermediate section 52; and forward section 54. Rear section 50 is generally in the form of a cylinder having a diameter $D_{10}$, with a substantially flat rear surface 56, and chamfered rear edges 58. Edges 58 are suitably chamfered to approximately 45° to a distance of approximately 0.64 mm, to facilitate insertion of insert 30 into lipped chamber 35, as will be explained. Diameter $D_{10}$ is maintained to relatively close tolerance, and suitably ranges from approximately 8 to 15 mm, preferably approximately $11.56 \pm 0.03$ mm for a small, or $12.5 \pm 0.03$ mm for a large, component.

Intermediate section 52 is also cylindrical, with a predetermined diameter $D_{11}$, less than diameter $D_{10}$ of first section 50, and predetermined axial height $D_{12}$. Diameter $D_{11}$ suitably ranges from approximately 11 to 13.5 mm, preferably 11.66 mm for a small unit, or 13.08 mm for a large unit. Axial height $D_{12}$ is maintained to close tolerance, suitably 0.81 mm $-0$, $+0.13$ mm for both large and small components.

Forward section 54 suitably includes a cylindrical land 54A merging with an integral frustro-conical section 54B, which presents beveled forward peripheral side 42 of insert 30. As previously noted, periphery 42 is beveled to a predetermined angle $\theta_1$, preferably on the order of 30°. Land 54A is suitably of a predetermined diameter $D_{13}$, greater than diameter $D_{10}$ of first section 50, and height $D_{14}$ (FIG. 3C). Diameter $D_{13}$ suitably ranges from approximately 10 to 16 mm, preferably approximately 13.11 mm for a small unit, or 14.15 mm for a large unit. Height $D_{14}$ is suitably on the order of 0.4 mm, preferably 0.38 mm for both large and small components. Forward section 54 manifests a predetermined aggregate height $D_{15}$. Height $D_{15}$ suitably ranges from approximately 1 to 2 mm, preferably 1.63 mm for a small unit, or 1.47 mm for a large unit.

Figure 3B:
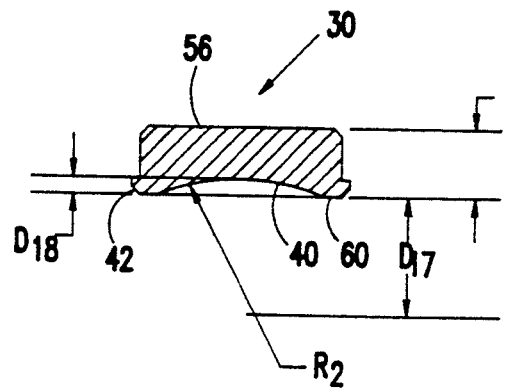
Figure 3C:
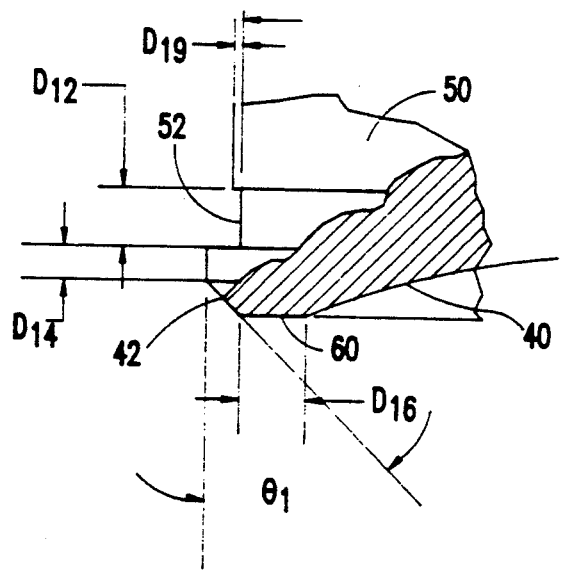
FIG. 3C is a detail view of the peripheral bevel of the insert of FIGS. 3A and 3B.
Figure 4C:
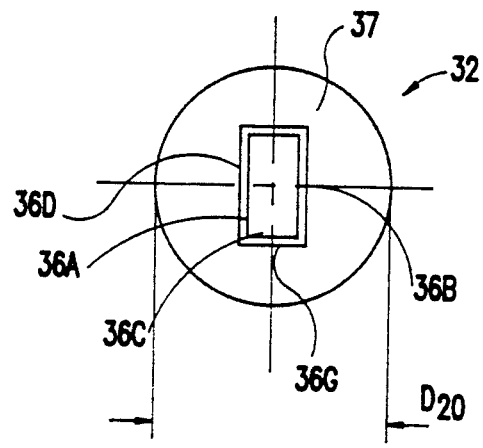
FIGS. 4A, 4B and 4C are cross-sectional front, side, and bottom views of the phalangeal base unit of the system of FIG. 1.
Figure 4A:
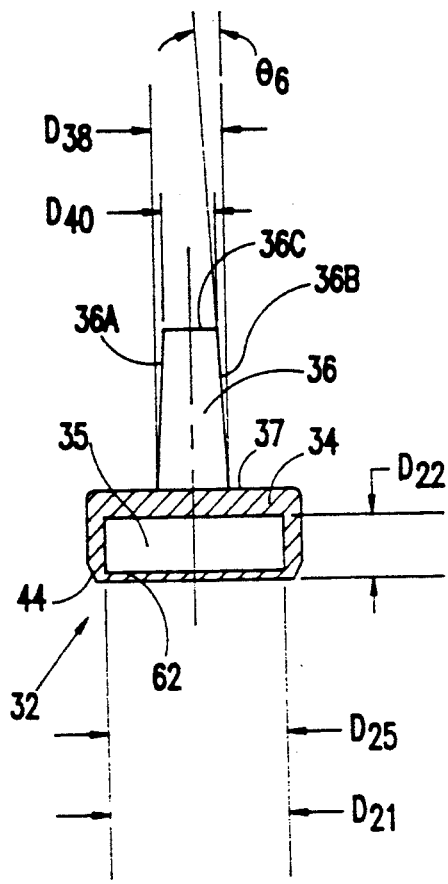
Figure 4B:
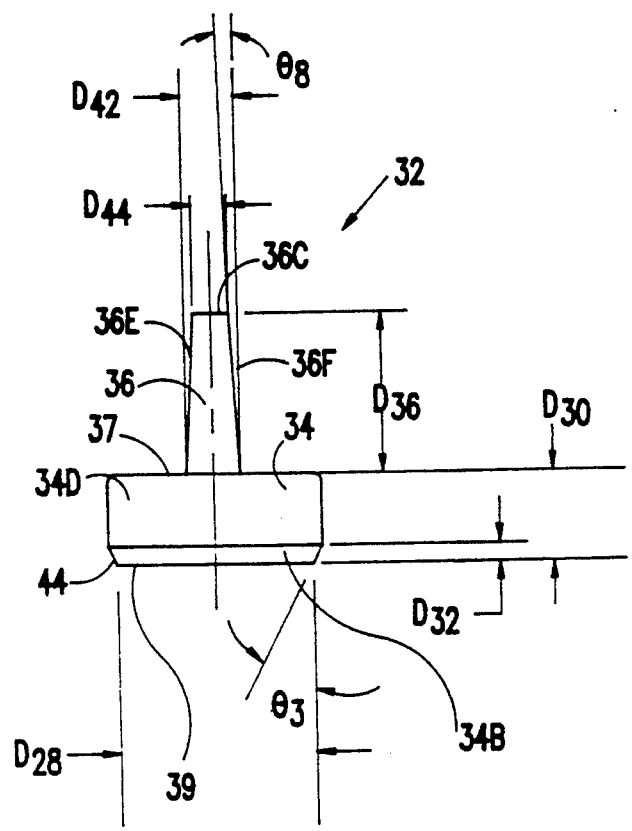
Figure 4D:
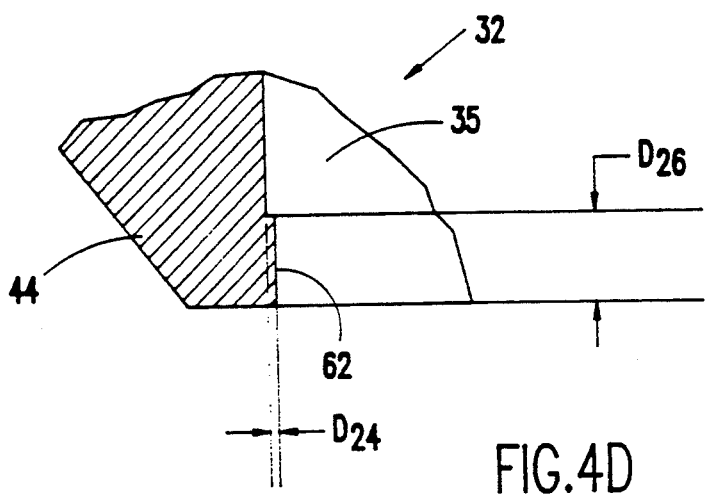
FIG. 4D is a cross-sectional detail view of the periphery of the phalangeal component of FIGS. 4A, 4B and 4C.

As best seen in FIGS. 3B and 3C, concave bearing surface 40 is formed in the face of frustro-conical section 54, centrally disposed and bounded by a thin concentric peripheral land 60 of a predetermined width $D_{16}$. Width $D_{16}$ is suitably on the order of 0.5 mm, and preferably 0.51 mm, for both small and large units.

Surface 40 is configured to cooperate with convex bearing surface 24, and is preferably in the form of a portion of the interior of a hollow sphere having a predetermined radius $R_2$, suitably approximating, and preferably equal to, the major radius $R_1$ of convex surface 24, with a center of curvature disposed on the central axis of insert 30 at a distance $D_{17}$ axially forward of the front surface of forward section 54. Distance $D_{17}$ suitably ranges from approximately 7.5 to 11.5 mm, preferably approximately 7.90 mm for a small unit, and 11.23 mm for a large unit. Thus, surface 40 forms a recess in the face of section 54 extending axially inward to a predetermined depth $D_{18}$, suitably ranging from approximately 1 to 2 mm, preferably 1.63 mm for a small unit, and 1.47 mm for a large unit. Rear section 50, intermediate section 52, and land 54A cooperate to form a peripheral recess in insert 30, of a depth $D_{19}$ (FIG. 3C) equal to the difference between diameters $D_{10}$ and $D_{11}$, suitably on the order of 0.05 mm, and preferably 0.06 mm.

Referring now to FIGS. 1, 4A, 4B, 4C and 4D, base unit 30 comprises, as noted above, receptacle portion 34, including forward opening chamber 35 and rear surface 37, and stem 36. Receptacle portion 34 includes a generally cylindrical rear portion 34A and an integral frustro-conical forward portion 34B. Rear portion 34B is of a predetermined outer diameter $D_{20}$ (FIG. 4C), a presents a generally flat, circular rear surface 37. Diameter $D_{20}$ is suitably somewhat smaller than diameter $D_1$ of metatarsal head 20, generally corresponding to the diameter of the resected end of bone 18, and suitably ranges from approximately 15 to 17.5 mm, preferably approximately 15.24 mm for a small unit, and 17.27 mm for a large unit. Forward portion 34B presents beveled forward peripheral side portion 44, which is chamfered to a predetermined angle $\theta_3$, preferably substantially equal to the chamfer angle of insert periphery 42, i.e., approximately 30°, and culminating at a forward face 39 of receptacle 34. Forward portion 34 manifests a predetermined axial height $D_{32}$ suitably ranging from approximately 1.25 to 2.5 mm, preferably 1.47 mm for a small unit, and 2.2 mm for a large unit. Receptacle 34 manifests a predetermined aggregate axial height of on the order of 5 mm, preferably 4.90 mm for both small and large units. Chamber 35 is disposed centrally in face 39, generally cylindrical in shape, of a predetermined diameter $D_{21}$, and extending inwardly to a predetermined depth $D_{22}$. Diameter $D_{21}$ generally corresponds to the diameter $D_{10}$ of rear section 50 of insert 30, suitably ranging from approximately 11.5 to 13 mm, preferably 11.88±3 mm for a small unit, and 12.62±3 mm for a large unit. Depth $D_{22}$ generally corresponds to the aggregate height $D_{23}$ (FIG. 3A) of sections 50 and 52 of insert 30. Depths $D_{22}$ and $D_{23}$ are preferably equal and maintained to close tolerance, suitably 3.63 mm −0, +0.13 mm.

A lip 62 is formed about the mouth of chamber 35 projecting radially inward a predetermined distance $D_{24}$ (FIG. 4D), suitably on the order of 0.1 mm, preferably 0.13 mm, such that the mouth of chamber 30 presents a circular opening of a predetermined diameter $D_{25}$ slightly greater than diameter $D_{11}$ of intermediate portion 52 of insert 30, but smaller than diameter $D_{10}$ of rear section 50. Diameter $D_{25}$ suitably ranges from approximately 11 to 12.5 mm, preferably 11.43±0.03 mm for a small unit, and 12.37±0.3 mm for a large unit. The front face 39 of receptacle 34 is thus annular, with an inner diameter $D_{25}$ defined by lip 62, and an outer diameter $D_{28}$ (FIG. 4B) defined by the edge of chamfered side 44. Outer diameter $D_{28}$ suitably ranges from approximately 13 to 15 mm, preferably approximately 13.45 mm for a small unit and 14.73 mm for a large unit.

Lip 22 is of a predetermined axial height $D_{26}$, suitably 0.76 mm +0, −0.13 mm, closely corresponding to (slightly less than) the axial height $D_{12}$ of intermediate section 52 of insert 30, i.e., of the peripheral recess about insert 30. Lip 22 is employed to retain insert 30 in chamber 35.

Insert 30 snap-fits into chamber 35 with concave surface 40 outward and forward section 54 maintained exteriorly of the chamber. Chamfered edges 58 of insert 30 cause rear surface 56 to be of a slightly lesser diameter than diameter $D_{25}$ of the mouth of chamber 35, facilitating insertion of rear section 50 into chamber 35. Insert 30 is sufficiently resilient to permit rear section 50 to compress to pass lip 62. Lip 62 ultimately engages the peripheral recess in insert 30 at intermediate section 52. Thus, when insert 30 is fully received in chamber 35, rear surface 56 of insert 30 abuts the rear interior surface of chamber 35, and the rear surface of insert forward section 54 abuts receptacle front surface 39, overlying lip 62.

Stem 36 extends axially rearward from rear surface 37 of receptacle 34 a predetermined distance $D_{36}$ (FIG. 4B) suitably ranging from approximately 11 to 13 mm, preferably approximately 11.07 mm for a small, and 12.7 mm for a large, component. Stem 36 is preferably generally centered on rear surface 37 and exhibits a rectangular cross-section that decreases with distance from the juncture with rear surface 27. The projection of stem 36 in the frontal plane (FIG. 4A) is a generally wedge-shaped quadrilateral formed by respective opposing sides 36A and 36B, and end 36C and a juncture 36D with rear surface 37. Juncture 36D is of a predetermined width $D_{38}$ suitably ranging from approximately 5 to 7 mm, preferably approximately 5.59 mm for a small, and 6.60 mm for a large, component. Sides 36A and 36B each taper inwardly by a predetermined angle $\theta_6$, preferably on the order of 3.5° for both large and small components such that the projection of end 36C is of a lesser predetermined width $D_{40}$, suitably ranging from approximately 4 to 5.5 mm, preferably approximately 4.22 mm for a small, and 5.08 mm for a large, component.

The projection of stem 36 in the coronal plane (FIG. 4B) is likewise a generally wedge-shaped quadrilateral, formed of respective opposing sides 36E and 36F, end 36C, and a juncture 36G with rear surface 37. Juncture 36G presents a predetermined width $D_{42}$, suitably ranging from approximately 3.5 to 5 mm, preferably approximately 3.61 mm for a small, and 4.57 mm for a large, component. Sides 36E and 36F each taper inwardly by a predetermined angle $\theta_8$, suitably ranging from 2.5° to 4°, preferably approximately 2.8° for a small, and 3.4° for a large, component. The projection of end 36C presents a predetermined width $D_{44}$, suitably ranging from approximately 2 to 3.5 mm, preferably approximately 2.54 mm for a small, and 3.05 mm for a large, component.

The various portions of the exterior of metatarsal component 12 and phalangeal base unit 32 are treated to selectively promote, or inhibit, bony ingrowth. Specifically, the surfaces of stems 22 and rear surfaces 27 and 37 are textured (roughened), suitably employing a 5-micron grit blast, to promote bony ingrowth to enhance bonding of the components to the bones. In contradistinction, land 26 of metatarsal component 12 and the side surfaces of phalangeal receptacle 34 are polished (in the manner of bearing surface 24) to inhibit bony overgrowth.

Figure 2D:
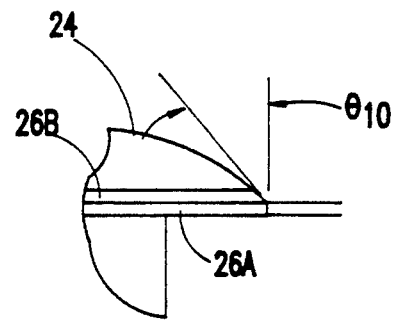
FIG. 2D is a partial front view of a second embodiment of a metatarsal component.

In some instances, it is desirable to include provisions to facilitate lubrication between bearing surfaces 24 and 40 by natural intercapsular synovial fluid, to reduce friction between, and concomitant wear on, the bearing surfaces. Referring to FIG. 2D, this is accomplished by including a frustro-conical portion as part of the intermediate portion of metatarsal head 20, disposed to extend transversely beyond bearing surface 24. More specifically, a cylindrical land 26A merges with a frustro-conical section 26B, which in turn merges with bearing surface 24. Frustro-conical section 26B is suitably disposed at a predetermined angle $\theta_{10}$, and presents an axial height on the order of 0.5 mm, preferably approximately 0.40 mm for both small and large components. Angle $\theta_{10}$ suitably approximates, but is slightly less than, the tangent to bearing surface 24 at the juncture with frustro-conical section 26B.

With reference to FIGS. 1 and 2D, during extremes of flexion and extension, the edge of phalangeal component 14 overhangs bearing surface 24 by a predetermined limited amount corresponding to the transverse width of frustro-conical section 26B. Since frustro-conical section 26B is disposed transversely beyond bearing surface 24 and manifests an angle less than the tangent to bearing surface 24, concave bearing surface 40 is separated from frustro-conical section 26B by a small space, permitting the introduction of intercapsular synovial fluid under surface 40. If desired, a shallow channel (not shown) can be formed in concave bearing surface 40 to further facilitate lubrication. The relative dimensions of the components are offset such that even in the extremes of flexion and extension, concave bearing surface 40 never extends transversely beyond land 26A, and impingement with anatomical structures and possibly bony overgrowth is avoided.

Figure 2E:
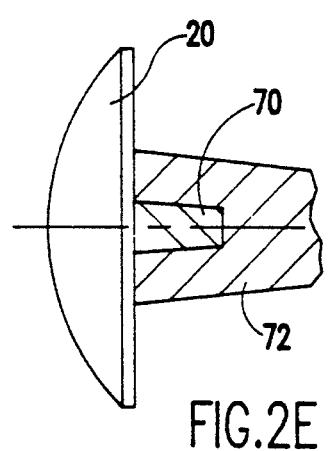
FIG. 2E is a partial sectioned front view of a third embodiment of a metatarsal component.

As previously mentioned, phalangeal base unit 32 is formed of titanium. The use of titanium is particularly advantageous in that titanium is extremely biocompatible and amenable to texturing, e.g., by grit blasting, to promote bony ingrowth to hold the component securely in place in bone 18. For those reasons, it would also be desirable to form metatarsal component 20 of titanium. However, titanium does not provide an optimum bearing surface for polyethylene. Accordingly, bearing surface 24 (and hence the entirety of metatarsal head 20 when a unitary component) is formed of cobalt chrome. It is also desirable to employ, in some situations, stems of varying configurations, e.g., longer, wider, narrower, at angles varying from the norm, etc. Accordingly, components 12 and 14 can be made to engage stem sleeves of varying configuration to accommodate varying situations. Referring to FIG. 2E, a metatarsal head 20, formed of cobalt chrome, includes a short tang 70. Tang 70 is slightly tapered, and is received in a conforming channel in the end of a stem sleeve 72, suitably formed of textured titanium, manifesting a desired configuration. The channel in stem sleeve 72 has an angle slightly shallower than the taper of tang 70, so that a secure press fit is effected between head 20 and sleeve 72.

It will be understood that the above description is of preferred exemplary embodiments of the present invention, and the invention is not limited to the specific forms shown. Modifications may be made in the design and arrangement of the elements within the scope of the invention, as expressed in the claims.

We claim:

1. A non-constrained total joint system for effecting an articulation between first and second adjacent resected bony shafts, the system comprising:
  A. a first component formed of non-plastic biocompatible material and including:
    (a) a first stem configured to be received in the end of said first bony shaft;
    (b) a convex bearing surface, said convex bearing surface extending up to 180°; and
    (c) means, including a non-bearing intermediate portion interposed between said first stem and said convex bearing surface, for fixedly attaching said convex bearing surface transversely to said first bony shaft, said non-bearing intermediate portion comprising a cylindrical portion adjacent to said first stem and a frustro-conical portion adjacent to said convex bearing surface, said frusto-conical portion providing for sufficient clearance for articulation of the joint system and protecting said convex bearing surface against possible boney overgrowth;
  B. a second component, including:
    (a) a second stem adapted to be received in the end of said second bony shaft;
    (b) a receptacle portion attached to said second stem; and
    (c) an intermediate insert formed of a biocompatible plastic, fixedly disposed in said receptacle portion, said insert including a concave bearing surface conforming to said convex bearing surface and of an area significantly less than the area of said convex bearing surface.

2. The system of claim 1 wherein said frustro-conical portion manifests an angle that is no greater than the tangent to said convex bearing surface at the juncture of said convex bearing surface and said frustro-conical portion.

3. A non-constrained total joint system for effecting an articulation between first and second adjacent resected bony shafts, the system comprising:
  a first component composed of a unitary, non-plastic biocompatible material and formed as an integral head and rearwardly projecting first stem, said first stem configured to be received in the end of said first bony shaft, said head having a convex bearing surface having a large major radius of curvature relative to a diameter of said head and approximating that of the anatomic articulating surface and extending up to 180°, said head further having a non-bearing intermediate portion interposed between said first stem and said convex bearing surface to offset said convex bearing surface from the end of said first bony shaft by a distance which provides sufficient clearance for articulation of the joint system and protecting said convex bearing surface against possible boney overgrowth;

a second component, including an integral receptacle portion and a rearwardly projecting second stem, said second stem configured to be received in the end of said second bony shaft, said receptacle portion being substantially cylindrically shaped with an outer first beveled surface and receiving an intermediate insert formed of a biocompatible plastic, fixedly disposed within said receptacle portion, said insert including a concave bearing surface conforming to said convex bearing surface and of an area significantly less than the area of said convex bearing surface, said intermediate insert projecting beyond said receptacle portion and having a second beveled surface intersecting with said concave bearing surface and substantially forming an extension of said first beveled surface and protecting said concave bearing surface against possible boney overgrowth.

4. The non-constrained total joint system of claim 3 wherein said intermediate insert is formed of ultrahigh molecular weight polyethylene.

5. The non-constrained total joint system of claim 4 wherein said integral receptacle portion and said second stem are formed of titanium.

6. The non-constrained total joint system of claim 5 wherein said first component is formed of cobalt chrome.

7. The non-constrained total joint system of claim 3 including means for effecting a snap fitting of said intermediate insert in said receptacle portion.

8. The non-constrained total joint system of claim 3 wherein said first and second stems have a generally rectangular cross-section.

9. The non-constrained total joint system of claim 3 wherein the surface of said first beveled surface is at an angle within the range of 20° to 35° relative to the axis of said receptacle portion.

10. The non-constrained total joint system recited in claim 3 wherein said major radius of curvature is in the range of from approximately 7 to 17 mm and said distance is in the range of from approximately 0.5 to 1.5 mm.

11. A non-constrained total joint system for effecting an articulation between first and second adjacent resected bony shafts, the system comprising:

a first component composed of a unitary, non-plastic biocompatible material and formed as an integral first head and rearwardly projecting first stem, said first stem configured to be received in the end of said first bony shaft, said head having a convex bearing surface having a large major radius of curvature relative to a diameter of said head and approximating that of the anatomic articulating surface and extending up to 180°, said head further having a non-bearing intermediate portion interposed between said first stem and said convex bearing surface to offset said convex bearing surface from the end of said first bony shaft by a distance which provides sufficient clearance for articulation of the joint system and protecting said convex bearing surface against possible boney overgrowth;

a second component, including a second head attached to a rearwardly projecting second stem, said second stem configured to be received in the end of said second bony shaft, said second head being substantially cylindrically shaped with an outer beveled surface, said second head including a concave bearing surface formed of a biocompatible plastic conforming to said convex bearing surface and of an area significantly less than the area of said convex bearing surface, said beveled surface intersecting with said concave bearing surface and protecting said concave bearing surface against possible boney overgrowth.

12. The non-constrained total joint system of claim 11 comprising means for fixedly attaching said concave bearing surface to said second stem including a base formed of a non-plastic biocompatible material integral with said second stem, and having a recessed portion configured to receive at least a portion of said biocompatible plastic therewithin.

13. The non-constrained total joint system of claim 12 wherein said biocompatible plastic is ultrahigh molecular weight polythylene.

14. The non-constrained total joint system of claim 11 wherein said outer beveled surface is frustro-conical.

* * * * *